(12) United States Patent
Hong et al.

(10) Patent No.: US 6,833,461 B2
(45) Date of Patent: Dec. 21, 2004

(54) PROCESS FOR PREPARING SIMVASTATIN

(75) Inventors: Chung Il Hong, Chicago, IL (US); Jung Woo Kim, Seoul (KR); Hee Jong Shin, Boocheon (KR); Tae Won Kang, Seoul (KR); Dong Ock Cho, Suwon (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 0 days.

(21) Appl. No.: 10/468,852

(22) PCT Filed: Feb. 27, 2001

(86) PCT No.: PCT/KR01/00301

§ 371 (c)(1),
(2), (4) Date: Aug. 25, 2003

(87) PCT Pub. No.: WO01/45484

PCT Pub. Date: Jun. 28, 2001

(65) Prior Publication Data

US 2004/0068123 A1 Apr. 8, 2004

(51) Int. Cl.$^7$ .............................................. C07D 309/30
(52) U.S. Cl. ...................................................... 549/292
(58) Field of Search ......................................... 549/292

(56) References Cited

U.S. PATENT DOCUMENTS 4,444,784 A * 4/1984 Hoffman et al. ............ 514/460

OTHER PUBLICATIONS

Corey et al, JACS, vol. 94(17), p.6190–6191(1972).*

* cited by examiner

*Primary Examiner*—Bernard Dentz
(74) *Attorney, Agent, or Firm*—Finnegan, Henderson, Farabow, Garrett & Dunner, LLP

(57) ABSTRACT

The present invention relates to an improved process for preparing simvastatin and more particularly, the improved process for preparing simvastatin expressed by formula 1 with high yield and high purity by performing the following sequential processes comprising: (i) hydrolysis of lovastatin as starting material with potassium t-butoxide in an organic solvent and small amount of water under a mild reaction condition, followed by lactonization of the obtained solid intermediate with preventing from formation of by-products; (ii) protection of an alcohol group with t-butyldimethylsilyl group which can be easily removed with concentrated hydrochloric acid without the formation of by-products; (iii) acylation of the obtained protected intermediate with acyloxytriphenyl phosphonium salt as an acylating agent under a mild reaction condition; and (iv) removal of the silyl protective group with a concentrated hydrochloric acid. The present invention is to provide the improved process of preparing simvastatin expressed by formula 1 environmentally sound, economically efficient, and industrially useful.

9 Claims, No Drawings

PROCESS FOR PREPARING SIMVASTATIN

This application is a 371 of PCT/KR01/00301 filed Feb. 27, 2001.

BACKGROUND OF THE INVENTION

Field of the Invention

The present invention relates to an improved process for preparing simvastatin and more particularly, the improved process for preparing simvastatin expressed by formula 1 with high yield and high purity by performing the following sequential processes comprising:

(i) hydrolysis of lovastatin as starting material with potassium t-butoxide in an organic solvent and small amount of water under a mild reaction condition, followed by lactonization of the obtained solid intermediate with preventing from formation of by-products;

(ii) protection of an alcohol group with t-butyldimethylsilyl group which can be easily removed with concentrated hydrochloric acid without the formation of by-products;

(iii) acylation of the obtained protected intermediate with acyloxytriphenyl phosphonium salt as an acylating agent under a mild reaction condition; and (iv) removal of the silyl protective group with a concentrated hydrochloric acid.

The present invention is to provide the improved process of preparing simvastatin expressed by formula 1 environmentally sound, economically efficient, and industrially useful.

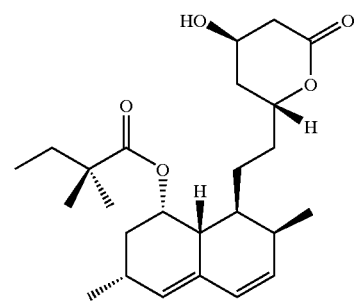
(1)

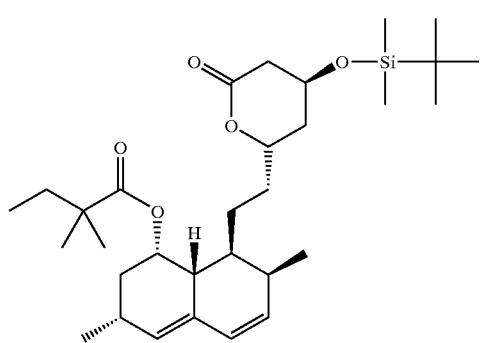
(2)

Simvastatin of formula 1 is known as antihypercholesterolemic agent that has excellent inhibitory activity of the HMG-Co A reductase and its preparing methods have been also intensively studied. General processes of preparing simvastatin of formula 1 include hydrolysis of lovastatin, lactonization, protection of an alcohol in lactone ring, acylation, and deprotection. Many patents are published with improved process for preparing simvastatin by characterizing each step of the process. Especially, purity of the product varies with the final deprotection step of the process.

When t-butyldimethylsily group is introduced as a protecting group to obtain the compound of formula 2, the deprotection reaction suffers from poor conversion to simvastatin due to formation of by-products such as compounds of formula 3 and formula 4.

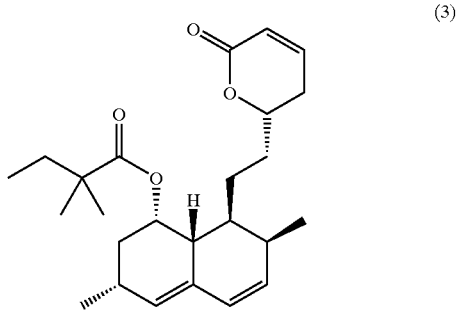
(3)

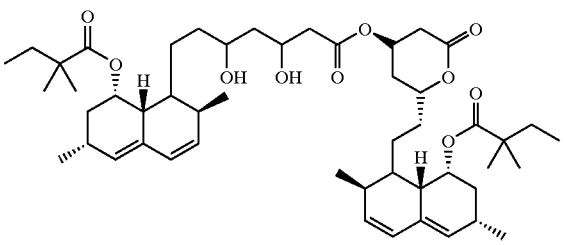
(4)

These by-products of the compounds 3 and 4 cannot be easily removed by conventional purifications and thus it affects yield and purity of the final product, simvastatin. Use of t-butylammonium fluoride (TBAF) or hydrogen fluoride (HF) having fluoro anion (F$^-$) in the deprotection of t-butyldimethylsily group in lactone ring have been reported [*J. Org. Chem.* 1991, 56, 4929–4932]. However, as shown in scheme 1, the by-product of formula 3 can be generated during prolonged reaction due to a reaction between a fluoro ion (F$^-$) and an acidic α-proton of the compound of formula 2. Yield of said deprotection with TBAF is 72% [*J. Org. Chem.* 1991, 56, 4929–4932].

Scheme 1

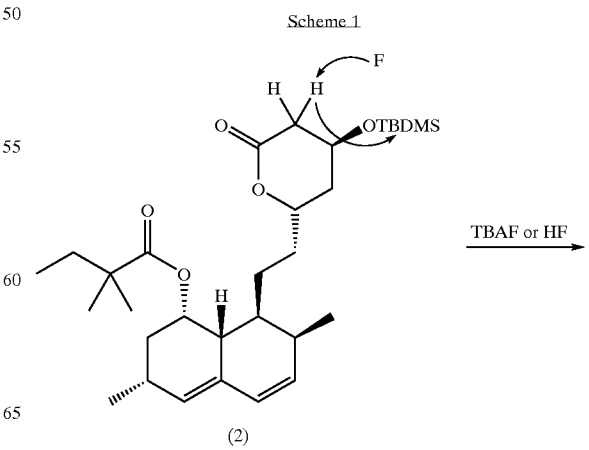
(2)

3
-continued

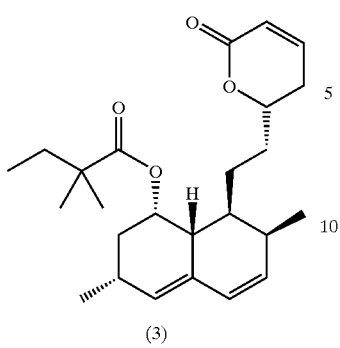

(3)

U.S. Pat. No. 4,845,237 and Korean Patent No. 133,599 disclose that 0.4–0.8% of the compounds 3 and 4 as by-products are produced during the reaction, resulting decrease in purity.

Another process for preparing simvastatin of formula 1 introduces ring-opening of lactone ring to amide group in order to solve the problem for the formation of by-products as shown in scheme 2 [*J. Org. Chem.* 1991, 56, 4929–4932].

Scheme 2

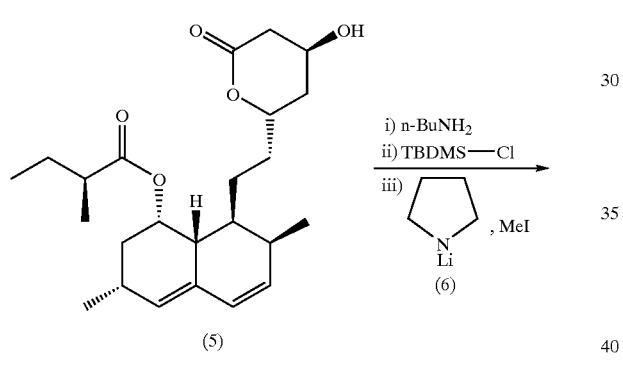

(5)

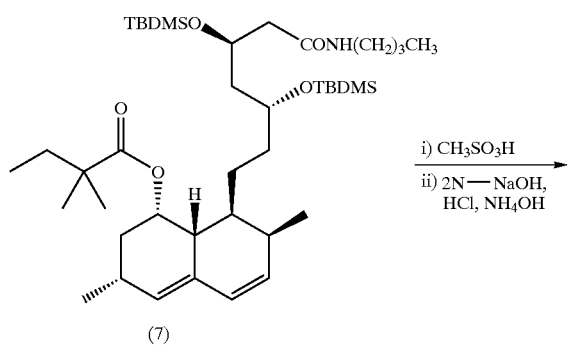

(7)

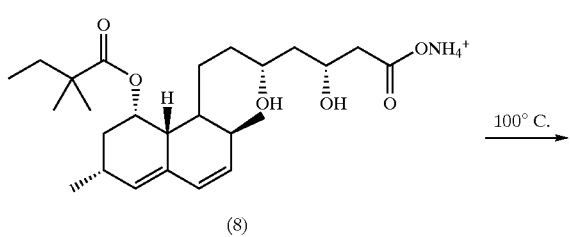

(8)

4
-continued

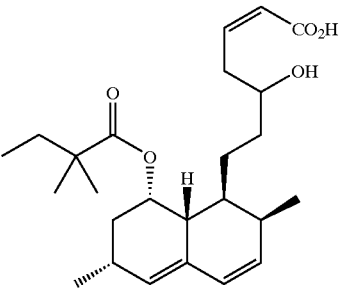

(1)

However, this process also have drawbacks: (i) in order to introduce a methyl group on α-position of substituted butylester group in the compound of formula 5, an unstable strong base such as a compound of formula 6, which is not appropriate in industrial scale, has to be used; (ii) a by-product such as a dehydrated unsaturated acid of the compound 9 which is precursor of the compound of formula 3 is produced during the hydrolysis of the compound of formula 7 and the following acidification with hydrochloric acid; (iii) since a high temperature is required to obtain the desired compound of formula 1 from the compound of formula 8, a dimer of the compound of formula 4 is produced as a by-product.

(9)

As described above, many processes still produce by-products such as the compound of formula 3 and the dimer compound of formula 4 and further, these by-products are not easily removed with conventional purifications, resulting low purity of simvastatin of formula 1.

In comparison of conventional removals of a protecting group, the process of scheme 1 is preferable in industrial scale to prepare simvastatin, but it requires improved method promising high yield and high purity without the formation of the by-products of the compounds 3 and 4.

And also, there are series of patents to prepare simvastatin of formula 1 from lovastatin as the starting material, it still requires improvement in hydrolysis and acylation.

SUMMARY OF THE INVENTION

As a result of that the inventors have long been engaged in the manufacture of simvastatin and have conducted intensive studies to resolve the drawbacks, the inventors have noted that introduction of t-butyldimethylsilyl (TBDMS) group as an alcohol protection group and construction of deprotection reaction condition not to produce by-products of the compounds 3 and 4 promise highly pure production of simvastatin of formula 1 in high yield.

The present invention is also characterized by the process for preparing from lovastatin to simvastatin, wherein the process is performed under mild condition and by using reagents which are easy handle and industrially useful.

Therefore, an object of the present invention is to provide an economical and efficient process for preparing simvastatin of formula 1 which is useful as the antihypercholesterolemic agent in industrial scale.

DETAILED DESCRIPTION OF THE INVENTION

The present invention is characterized by preparing simvastatin of formular 1 by deprotecting t-butydimethylsilyl protected intermediate of formular 2 with concentrated hydrochloric acid in one or mixed solvent selected from the group consisting of tetrahydrofuran, 1,3-dioxane, 1,4-dioxane, methoxyethane and diethyl ether.

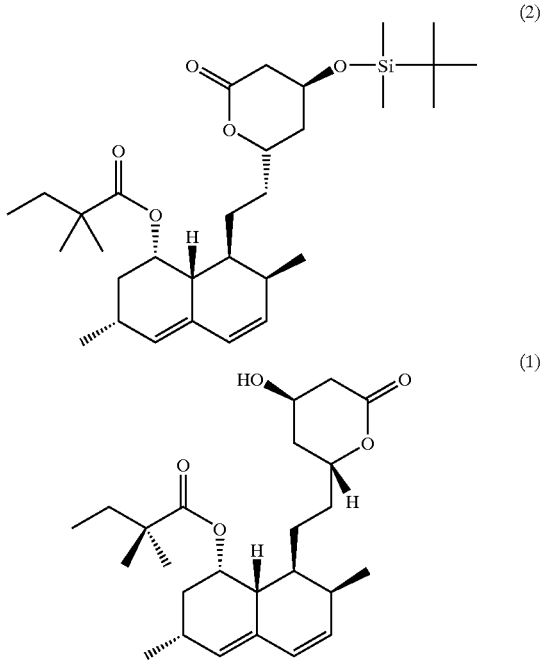

The present invention is described in more detail hereunder.

The present invention provides the process for preparing simvastatin of formula 1 through the deprotection using a concentrated hydrochloric acid in a selected solvent and the following crystallization of the obtained simvastatin is performed to produce high yield(92%) and high purity (99.5%; area ratio of HPLC) of the final product.

The deprotection of the present invention is carried in such a manner that the concentrated hydrochloric acid is added to a solution containing the compound of formula 2 at −5 to 10° C. for 6 to 7 hrs. In the deprotection of the compound of formula 2 to the compound of formula 1, there is no formation of by-products.

According to the inventors, yield and purity of simvastatin varies with reaction conditions (i.e., kind of acid, amount of acid, solvent, temperature, reaction time, and the like) in the deprotection of TBDMS protected intermediate of formula 2.

Examples of the acid are concentrated hydrochloric acid, diluted hydrochloric acid (diluted concentrated hydrochloric acid with distilled water), acetic acid, nitric acid, sulfuric acid, hydrofluoric acid, methanesulfonic acid, and p-toluenesulfonic acid. In the use of acetic acid or p-toluenesulfonic acid, the reaction was not occurred at all. In the use of nitric acid, sulfuric acid or methanesulfuric acid, the starting material was disappeared with time but only, by-products which were impossible to identify were produced without any formation of the product, simvastatin. In the use of hydrofluoric acid or diluted hydrochloric acid, simvastatin was produced with not enough purityn due to the formation of by-products of the compounds 3 and 4. On the other hand, in the use of concentrated hydrochloric acid, simvastatin was produced in high purity and high yield without the formation of by-products. Thus, concentrated hydrochloric acid is the most preferable in the deprotection.

For the preferred reaction conditions, amount of concentrated hydrochloric acid is 5–10% (v/v) to a reaction solvent used, a reaction time is 6–7 hrs and a temperature is −5–10° C. A reaction solvent is one or more selected from the group consisting of tetrahydrofuran, 1,3-dioxane, 1,4-dioxane, methoxyethane and diethyl ether. A preferred solvent is a mixture of tetrahydrofuran and 1,4-dioxane (mixed ratio of 0–100:100–0) and more preferred ratio thereof is 95:5.

After the deprotection, the obtained simvastatin is crystallized by the following process: (i) dissolving in ethyl acetate at 40–60° C.; (ii) adding n-hexane; and (iii) cooling to room temperature to give simvastatin in high purity, (99.5%) and high yield (92%). An expected reason of obtaining high pure simvastatin in crystallization process is no formation of by-products of the compounds 3 and 4, which are relatively unstable downy crystals and thus interfere in crystallization of simvastatin.

Conventional methods in the preparation of simvastatin produce by-products of the compounds 3 and 4 in the deprotection which affect crystallization and thus, lower the yield and purity of the final product, while that of the present invention does not produce by-products in the deprotection carried with concentrated hydrochloric acid and thus, highly pure simvastatin (99.5%, area ratio of HPLC) is produced after crystallization in high yield (92%).

The present invention is also characterized by the following sequential process comprising; hydrolysis of lovastatin as the starting material, lactonization, protection of an alcohol on the lactone ring, acylation and deprotection under appropriate reaction conditions to obtain simvastatin of formula 1.

The manufacturing process of preparing simvastatin from lovastatin as the starting material is described in scheme 3:

(i) Hydrolysis of lovastatin of formula 10 with potassium t-butoxide, organic solvent and small amount of water at a temperature of from −60 to 25° C.;

(ii) Lactonization of the hydrolysed intermediate of formula 11 in an organic solvent in the presence of an acid catalyst;

(iii) Protection of an alcohol group of the compound of formula 12 to t-butyldimethylsilyl(TBDMS) protected intermediate of formula 13 with a silylating agent in the presence of base;

(iv) Acylation of the compound of formula 13 with acyloxytriphenylphosphonium salt of formula 14 in the presence of base at a temperature of 0–25° C.; and (v) Deprotection of the acylated compound of formula 2

Scheme 3

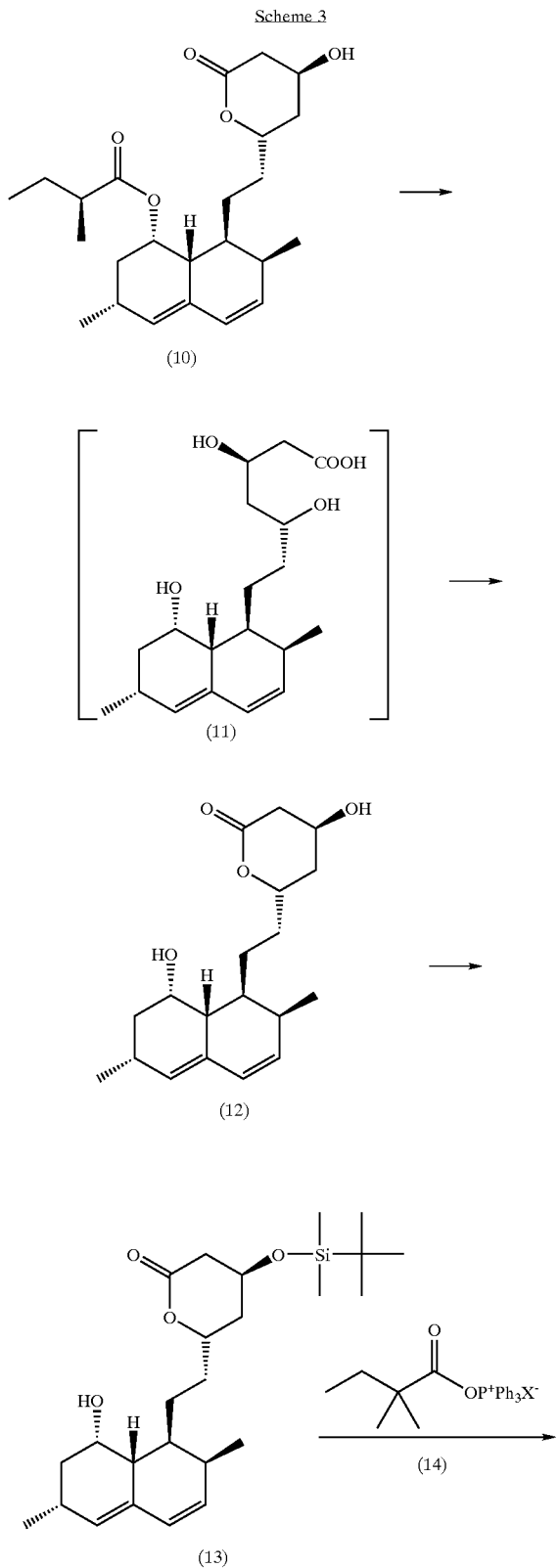

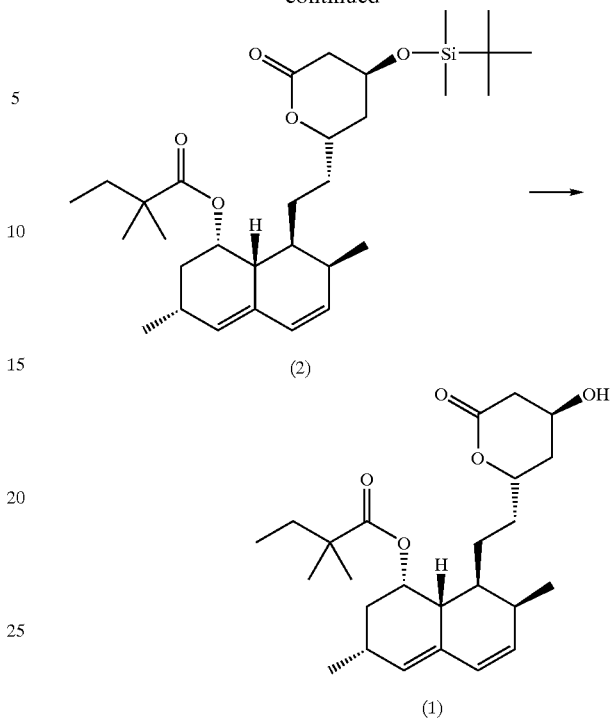

wherein X represents a halogen atom.

Hereunder is given the more detailed description of the manufacturing process of scheme 3.

In the hydrolysis of the present invention, lovastatin which is known compound of formula 10 is reacted with potassium t-butoxide and small amount of water at a temperature of from −60 to 25° C. for 8 hrs in an organic solvent to give the compound of formula 11 in high yield (94%). Said organic solvent in the hydrolysis is diethylether, dimethoxyethane or tetrahydrofuran, preferably tetrahydrofuran. 3–10 equivalents of potassium t-butoxide is used to lovastatin of formula 10, preferably 5–8 equivalents, most preferably 8 equivalents. Addition of small amount of water is important in the hydrolysis because water reacts with potassium t-butoxide to generate OH⁻ which is required to open ester ring of the compound of formula 10. If amount of water is too small or too much, the hydrolysis does not proceed completely. Therefore, 2–4 equivalents of water to lovastatin of formula 10 is preferred, most preferably 2.2 equivalents. Unlike known conventional hydrolysis using LiOH in aqueous solution, the hydrolysis of the present invention produces the solid compound of formula 11 and thus, it can be possible to remove completely 2-methylbutyric acid which is a by-product. Therefore, the yield can be maximized with the obtained solid compound of formula 11 in the lactonization by preventing esterification between molecules by 2-methylbutyric acid.

The solid compound of formula 11 can be lactonized by known methods refluxing in toluene or in the presence of acid catalyst in organic solvent at room temperature to produce the lactonized compound of formula 12 in high yield (98%). Solvent used in lactonization is one or more selected from the group consisting of toluene, dichloromethane, ethyl acetate, acetonitrile and diethyl ether. Acid used is p-toluenesulfonic acid, methanesulfonic acid or trifluoroacetic acid. And then, the lactonized compound of formula 12 can be isolated for the next reaction or directly used for the next silylation without isolation thereof.

An alcohol group on the lactone ring of the compound 12 can be silylated with t-butyldimethylsilyl chloride to obtain the silyl group protected intermediate of formula 13 in high yield (95%). In order to protect the alcohol group selectively, 1–4 equivalents of t-butyldimethylsilyl chloride is used in an organic solvent in the presence of base. The base used in the protection reaction is imidazole, pyridine, triethylamine or morpholine and the organic solvent used is acetonitrile, dichloromethane, or chloroform, preferably dichloromethane.

The obtained compound of formula 13 is then acylated with acyloxytriphenylphosphonium salt in an organic solvent and under a mild condition in the presence of base to produce the compound of formula 2 without any formation of by-products in high yield (97%). The organic solvent used in the acylation is dichloromethane, tetrahydrofuran, diethyl ether, acetonitrile, ethyl acetate or acetone, preferably dichloromethane. The base used is pyridine, triethylamine, imidazole, morpholine or 2,6-lutidine. The reaction is preferred to carry in a temperature of from −30 to room temperature and under anhydrous condition.

Acyloxytriphenylphosphonium salt of formula 14 used in the acylation is prepared by activating 2,2-dimethylbutyric acid with triphenylphophine and halogenation agent as shown in Scheme 4, Scheme 4

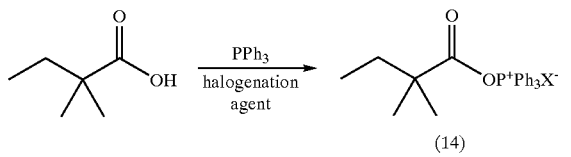

(14)

wherein X represents a halogen atom.

N-haloimide is preferred as the halogenation agent in the reaction of Scheme 4 and examples thereof include N-chlorosuccinimide, N-iodosuccinimide, N-bromosuccinimide, N-chlorophthalimide, N-iodophthalimide, N-bromophthalimide, N-bromoacetamide, and 1,3-dibromo-5,5-dimethylhydantoin.

The obtained acylated compound of formula 2 is deprotected and crystallized to produce the desired compound simvastatin of formula 1 as described above. The deprotection and following crystallization are the most characteristic of the present invention.

When the process for preparing simvastatin from lovastatin is performed as described in the present invention, the total yield is over 80% which is much higher than that of the conventional processes. On top of that, another characteristic of the present invention is to produce simvastatin having high purity economically.

This invention herein is explained in more detail based on the following examples without limitations thereby.

EXAMPLE 1

Preparation of 7-[1',2',6',7',8',8a'(R)-hexahydro-2'(S),6'(R)-dimethyl-8'(S)-hydroxy-1'(S)-naphthyl]-3(R),5(R)-dihydroxy heptanoic acid To a mixed solution of 500 ml of tetrahydrofuran and 4.7 ml of water cooled to −30° C., was added 111 g of potassium t-butoxide, following 50 g of lovastatin. After the reaction mixture was stirred at room temperature for 5 hrs, it was cooled to 0° C. and 200 ml of water was added and concentrated. The reaction mixture was acidified to pH 2.0 with 6N HCl and stirred for 1 hr in cooled condition. The reaction mixture was filtered, washed with 100 ml of water and 100 ml of dichloromethane and then dried to obtain 39.3 g (94%) of white solid compound.

mp 127–128° C.;

IR(KBr) 3453, 3389, 1720, 1649 cm$^{-1}$;

$^1$H NMR (DMSO, 400 MHz) δ 0.79(d, J=6.9 Hz, 3H), 1.11(d, J=7.30 Hz, 3H), 1.10–2.36(m, 14H), 3.56(brs, 1H), 3.99(brs, 2H), 4.06(brs, 1H), 4.42(brs, 1H), 4.70(brs, 1H), 5.37 (brs, 1H), 5.68–5.73(m, 1H), 5.86(d, J=9.60 Hz, 1H), 11.96(brs, 1H).

EXAMPLE 2

Preparation of 6(R)-[2-[8'(S)-hydroxy-2'(S),6'(R)-dimethyl-1',2',6',7',8', 8a'(R)-hexahydronaphthyl-1'(S)]ethyl]-4(R)-hydroxy-3,4,5,6-tetrahydro-2H-pyran-2-on 10 g of triolic acid prepared in Exmple 1 was suspended into 100 ml of dichloromethane and 112 mg of p-toluenesuifonic acid was added and stirred for 1 hr at room temperature to complete lactonization. The reaction mixture was washed with saturated sodium bicarbonate solution, water and saturated brine and then dried and concentrated to give 9.2 g (97%) of the desired compound.

mp 127–128° C.;

IR(KBr) 3374, 2972, 2912, 1704 cm$^{-1}$; and $^1$H NMR (CDCl$_3$, 400 MHz) δ 0.89(d, J=7.0 Hz, 3H), 1.18(d, J=7.5 Hz, 3H), 1.40–2.75(m, 14H), 4.24(brs, 1H), 4.34–4.38(m, 1H), 4.68–4.73(m, 1H), 5.54(brs, 1H), 5.77–5.81(m, 1H), 5.97(d, J=9.60 Hz, 1H)

EXAMPLE 3

Preparation of 6(R)-[2-(8'(S)-hydroxy-2'(S),6'(R)-dimethyl-1', 2',6',7',8',8'a(R)-hexahydronaphthyl-1'(S))ethyl]-4(R)-(dimethyl-tert-butylsilyloxy)-3,4,5,6-tetrahydro-2H-pyran-2-on 9.2 g of the obtained lactonized compound was dissolved in 80 ml of dichloromethane and 8.0 g of imidazole and 8.9 g of t-butyldimethylsilyl chloride were added. The reaction mixture was stirred for 15 hrs at room temperature. The reaction mixture was washed with 5% of aqueous hydrochloric acid solution, water and saturated brine and then dried over anhydrous MgSO$_4$ and concentrated to produce the compound which is added into 200 ml of hexane and stirred at cooled condition for 1 hr and then filtered, washed with hexane and dried to give 12.3 g (95%) of the desired white solid compound.

mp 133–134° C.;

IR(KBr) 3483, 1712 cm$^{-1}$; and $^1$H NMR (CDCl$_3$, 400 MHz) δ 0.06(s, 3H), 0.07(s, 3H), 0.88(s, 9H), 0.89(d, J=7.22 Hz, 3H), 1.18(d, J=7.51 Hz, 3H), 1.48–2.60(m, 14H), 4.24(brs, 1H), 4.28–4.30(m, 1H), 4.66–4.69(m, 1H), 5.54(brs, 1H), 5.77–5.82(m, 1H), 5.97(d, J=9.64 Hz, 1H).

EXAMPLE 4

Preparation of 6(R)-[2-(8'(S)-2",2"-dimethylbutyryloxy-2'(S),6'(R)-dimethyl-1',2',6',7',8', 8'a(R)-hexahdronaphthyl-1'(S)ethyl)-4(R)-hydroxy-3,4,5,6-tetrahydro-2H-pyran-2-on 5.34 g of 2,2-dimethylbutyric acid was dissolved in 100 ml of dichloromethane and 13.3 g of triphenylphosphine was added and cooled to 0° C. After adding 8.6 g of N-bromosuccinimide, the reaction mixture was stirred for 30 min at room temperature to produce acyloxytriphenylphosphonium salt. After cooling the reaction mixture to 0° C., 5 g of the obtained compound prepared in Example 3 and 6.2 ml of N,N-dimethylaniline were added. The temperature was increased to room temperature and then the reaction mixture was stirred for 10 hrs at room temperature. The reaction mixture was washed with 5% of aqueous hydrochloric acid solution, water, saturated sodium bicarbonate solution, water and saturated brine and then concentrated to give cake which was added to 100 ml of hexane and stirred for 30 min at 0° C. The reaction mixture was filtered and the filtrate was concentrated to produce 6.0 g (97%) of the acylated oily compound. The compound was used for next reaction without further purification due to its high purity.

The acylated compound was dissolved in 48 ml of tetrahydrofuran and 2.5 ml of 1,4-dioxane. After the mixture was cooled to 0° C., 3.5 ml of concentrated hydrochloric acid was added and stirred for 6 hrs to complete the reaction. Triethylamine was added to adjust pH to 1.5 and then concentrated to dryness. And then 40 ml of ethyl acetate was added and washed with water and saturated brine. The ethyl acetate layer was dried over $MgSO_4$ and concentrated to give colorless cake. The cake was dissolved in 35 ml of dichloromethane and 0.07 g of p-toluenesulfonic acid was added and stirred for 1 hr at room temperature. The reaction mixture was concentrated and 15 ml of ethyl acetate was added and heated to 40–60° C. 60 ml of n-hexane was added slowly and then cooled to room temperature. After the reaction mixture was stirred for 1 hr, it was cooled to 0° C. and stirred again for 2 hrs to produce white precipitate which was filtered and dried. The obtained white solid was dissolved in 50 ml of methanol and small amount of activate carbon was added and stirred for 30 min. The activate carbon was removed by filteration and 50 ml of water was added to the filtrate and the mixture was cooled to 0° C. and stirred for 2 hrs to produce white precipitate. The precipitate was collected through filtration and dried under the vacuum to give 4.4 g (92%) simvastatin with high purity (over 99.5%, area ratio of HPLC).

mp 134–136° C.;

IR(KBr) 3552, 1730–1698 $cm^{-1}$; and $^1H$ NMR ($CDCl_3$, 400 MHz) δ 0.83(t, J=7.5 Hz, 3H), 0.88(d, J=7.0 Hz, 3H), 1.08(d, J=7.4 Hz, 3H), 1.12(s, 3H), 1.13(s, 3H), 1.20–1.96(m, 10H), 2.28–2.76(m, 6H), 4.37(m, 1H), 4.60(m, 1H), 5.36(m, 1H), 5.51(bt, J=3.3 Hz, 1H), 5.77(dd, J=6.1, 9.6 Hz, 1H), 5.98(d, J=9.6 Hz 1H).

Deprotection and crystallization reactions were performed with various acids as the same procedure of Example 4 and the results are shown in Table 1.

TABLE 1

| Category | Yield | Purity[1] | crystallity[2] | By-products |
|---|---|---|---|---|
| Conc. Hydrochloric acid | 92% | 99.5% | 5 | Below 0.3% |
| Acetic acid (75%) | — | — | — | No reaction |
| p-toluenesulfonic acid (95%) | — | — | — | No reaction |
| HF (50%) | 56–67% | 82–86% | 3 | More than 10% (more than 50 hr reaction) |
| TBAF | 60–65% | 85–92% | 3.5 | 1.6–15% (more than 26 hr reaction) |
| Nitric acid | — | — | — | No starting |

TABLE 1-continued

| Category | Yield | Purity[1] | crystallity[2] | By-products |
|---|---|---|---|---|
| (20–50%) | | | | material and no product |
| Sulfuric aicd (20–50%) | — | — | — | No starting material and no product |
| Methanesulfonic acid (20–50%) | — | — | — | No starting material and no product |
| Diluted hydrochloric acid (6N—HCl) | 40–60% | Higher than 85% | 3 | More than 15% (more than 50 hr reaction) |

[1]purity area ratio of HPLC
[2]crystallity: 5 (good)↔1 (bad)

Deprotection and crystallization reactions were performed with various organic solvents as the same procedure of Example 4 and the results are shown in Table 2.

TABLE 2

| Category | Yield | Purity[1] | Crystallity[2] | By-products |
|---|---|---|---|---|
| Tetrahydrofuran/ 1,4-dioxane (95/5, V/V) | 92% | 99.5% | 5 | Less than 0.3% (6–7 hrs of reaction time) |
| Methoxy ethane | 50% | Over 70% | 3 | Less than 5% (more than 10 hrs of reaction time) |
| Tetrahydrofuran | Over 90% | Over 92% | 5 | Less than 2% (3–4 hrs of reaction time) |
| 1,4-dioxane | Over 80% | Over 85% | 3.5 | Less than 3% (more than 10 hrs of reaction time) |
| 1,3-dioxane | Over 80% | Over 90% | 4 | Less than 5% (more than 10 hrs of reaction time) |

[1]Purity: area ratio of HPLC
[2]Crystallity: 5 (good)↔1 (bad)

The superiority of the present invention is showing in the Examples and further detailed description is followed hereunder.

First, in deprotection of the TBDMS protected intermediate of formula 2, conventional method is performed with tetrabutylammonium fluoride(TBAF)/acetic acid or HF for a long period (over 18 hrs) but it produces semi-pure-product in low yield (72%, overall yield of 48%) due to the formation of by-products such as the compounds of formulas 3 and 4. On the other hand, it is performed in a particular solvent such as tetrahydrofuran or 1,4-dioxane for much shorter time of 6–7 hrs to produce simvastatin without the formation of such by-products of the compounds 3 and 4 in high purity (over 99.5%) and high yield (92%).

Second, in the hydrolysis to produce the compound of formula 11, conventional method is performed for 56 hrs under a vigorous condition so that it produces irresistible by-products and further removal of 2-methylbutyric acid, which is another product during the reaction, is not possible because the hydrolyzed product is an oil. And thus, this 2-methylbutyric acid participates in esterification reactions between molecules so that the yield of this reaction cannot be higher than 81%. On the other hand, the hydrolysis of the present invention is performed for much shorter time of 8 hrs at a temperature of from −60 to 25° C. with minimizing the formation of by-products and further, the compound of formula 11 can be obtained in a solid state without containing 2-methylbutyric acid, resulting in no side reactions. Thus, the compound of formula 11 can be obtained in high yield of 94% in the hydrolysis of the present invention and the overall yield of preparing the compound of formula 12 is 92%.

Third, a typical solvent in the conventional protection reaction of an alcohol group is N,N-dimethylformaldehyde which is difficult to remove after the reaction so that the yield is around 69%, while the present invention uses an organic solvent which is easy to remove, resulting high yield of over 95%.

Fourth, the acylation of the conventional method requires the formation of acid chloride salt and have environmental problems such as the formation of sulfur dioxide and hydrochloric acid gas due to the use of thionyl cloride to produce acid chloride salt. However, that of the present invention is simply performed byt using very reactive acyloxyltriphenylphosphonium salt of formula 14 without producing acid chlorides. On top of that, it is profitable in industrial scale for performing the reaction in dichloromethane at a temperature of 0–25° C. in the present invention in stead of using poisonous pyridine at a high temperature of 100° C. in the conventional method. The overall yield of acylation and deprotection of the compound of formula 13 is 76% in the conventional method, while over 90% to produce the compound of formula 1 in the present invention.

As a result, the overall yield from lovastatin of formula 2 to simvastatin of formula 1 is 48% by the conventional process while over 80% by the present invention.

Therefore, the present invention is expected to provide the improved process of preparing simvastatin expressed by formula 1 which is efficient in the treatment of hyperlipemia in an industrial scale.

What is claimed is:

1. A process for preparing simvastatin of formula 1 by deprotecting t-butyldimethylsilyl protected intermediate of formula 2 with concentrated hydrochloric acid in one or mixed solvent selected from the group consisting of tetrahydrofuran, 1,3-dioxane, 1,4-dioxane, methoxyethane and diethyl ether

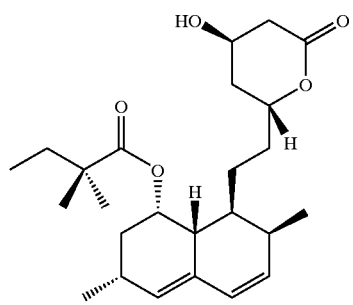

(1)

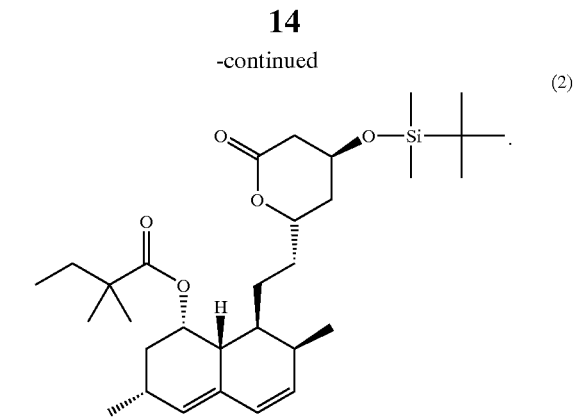

(2)

2. The process for preparing simvastatin according to claim 1, wherein said solvent is a mixture of tetrahydrofuran and 1,4-dioxane.

3. The process for preparing simvastatin according to claim 1, wherein said obtained deprotected compound is further crystallized by dissolving in ethyl acetate at 40–60° C. and adding n-hexane thereto.

4. The process for preparing simvastatin according to claim 1, wherein said protected compound of formula 2 is prepared by the following processes comprising:

(i) hydrolyzing lovastatin of formula 10 with potassium t-butoxide in an organic solvent and small amount of water at from −60 to 25° C. and further lactonizeing the hydrolyzed compound in an organic solvent in the presence of acid to produce the compound of formula 12;

(ii) protecting the alcohol group of the compound of formula 12 with t-butyldimethylsilyl group in the presence of base to produce the compound of formula 13; and (iii) acylating the compound of formula 13 with acyloxytriphenyl phophonium salt of formula 14 in the presence of base at a temperature of 0–25° C. to produce the compound of formula 2,

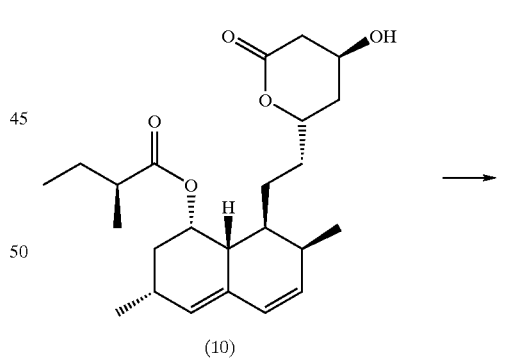

(10)

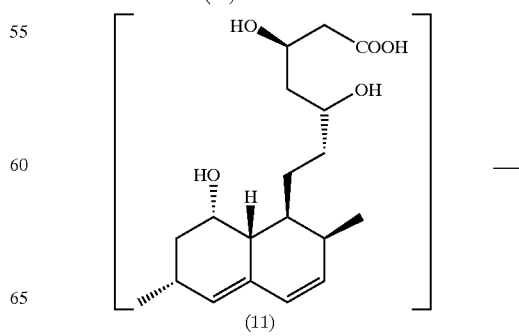

(11)

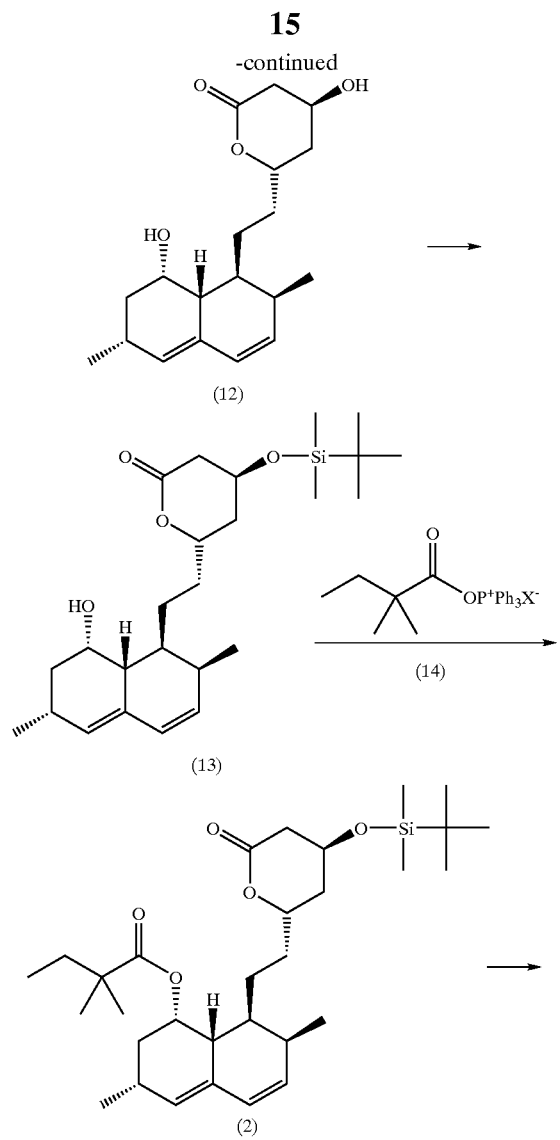
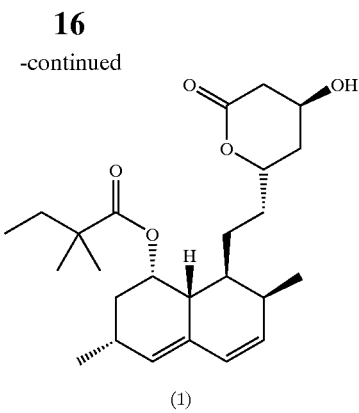

wherein X represents a halogen atom.

5. The process for preparing simvastatin according to claim 4, wherein said (i) hydrolysis is performed with potassium t-butoxide and 2–4 equivalents of water in tetrahydrofuran or diethyl ether.

6. The process for preparing simvastatin according to claim 4, wherein said (ii) protection is performed in dichloromethane.

7. The process for preparing simvastatin according to claim 4, wherein said acyloxytriphenylphosphonium salt in (iii) acylation is prepared by reacting 2,2-dimethylbutyric acid with triphenylphosphine and a halogenating agent.

8. The process for preparing simvastatin according to claim 7, wherein said halogenating agent is selected from the group consisting of N-bromoacetamide, N-bromosuccinimide, N-chlorosuccinimide, N-bromophthalimide, N-chlorophthalimide and 1,3-dibromo-5,5-dimethylhydantoin.

9. The process for preparing simvastatin according to claim 4, wherein said (iii) acylation is performed in an organic solvent selected from the group consisting of dichloromethane, tetrahydrofuran, toluene, and acetone.

* * * * *